United States Patent

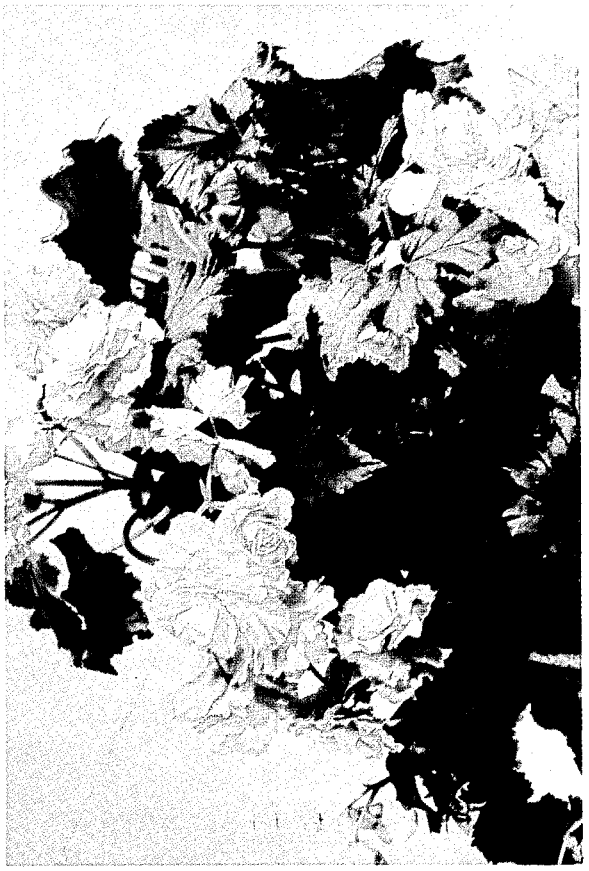

Plant Pat. 3,905
Patented June 8, 1976

3,905

BEGONIA PLANT

James C. Mikkelsen, Ashtabula, Ohio, assignor to Mikkelsens Inc., Ashtabula, Ohio Filed May 5, 1975, Ser. No. 574,628
Int. Cl. A01h 5/00
U.S. Cl. Plt.—68 1 Claim The present invention relates to a new and distinctive variety of begonia plant known by the cultivar name Elegance and botanically known as *Begonia elatior* (*hiemalis-Fotsch*). The new cultivar was discovered by me as a spontaneous sibling (one of three) mutation from a very bright deep rose red double flowering begonia identified by code number 8252 that was never commercialized. #8252 was a previous mutation from Aphrodite Rose, an unpatented commercial cultivar. Asexual reproduction by stem and leaf cuttings has reproduced the unique features of the new variety through successive propagations.

The following characteristics distinguish the new begonia from both its parent and other begonias commercially known and used in the floriculture industry:

1. Compared to deep rose red flowers of the parent variety, the flower color of Elegance is a very pleasing shade of light pink.

2. Compared to the parent variety, the flower size has increased from 7–8 cm. in diameter to 9–10 cm. in diameter.

3. The edges of the tepals are quite ruffled and center tepals are swirled, giving the flower a definite appearance of a camellia.

4. A unique characteristic of the individual flowers is the "flower-in-flower" effect giving added depth to the flowers as in azaleas. The flower separation may occur three or four times during the life of the flower. Flower depth often equals the diameter of the flower.

5. Compared to Rieger Aphrodite begonia types that are propagated mostly by vegetative top or stem cuttings, Elegance propagates extremely well by leaf cuttings that develop multiple adventitious shoots. This is of economic importance to propagators and growers of potted begonias.

6. In comparison to Rieger Aphrodite types Elegance has noticeably less flowers but this is offset by the unique form, size, and color of the flowers in Elegance.

7. The foliage is excellent in quality and immune to mildew.

8. The stems are more vigorous than those of Rieger Aphrodite types. Elegance can best be produced for uprights, and with proper handling for hanging baskets.

9. Flowering of Elegance is more consistent and definite under adverse environments than in Rieger Aphrodite types. Keeping quality is excellent.

The accompanying colored photograph illustrates the overall appearance of this variety taken as a face view of the plant and showing the colors as true as it is reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

Parentage: A spontaneous sibling mutation (one of three) that was found in begonia plant #8252 which was a mutation selected out of Aphrodite Rose.

Propagation: By vegetative top or stem cuttings that will root in 28 to 30 days. More effective control for flowering is by leaf cuttings that root in 30 to 35 days and eventually develop vegetative adventitious shoots from the base of the leaf petiole.

Rooting habit: Rooting time would be near average for this type of begonia, with roots that are fine, dendritic, numerous.

Plant form: A nearly upright bushy type of begonia that is easily grown for upright standards when properly supported and well adapted for baskets.

Habit of growth: Vigorous, fast growing, moderately self branching.

Blooming habits: Is quite free flowering in all seasons. Flowering response is often so complete that it is very difficult to obtain vegetative shoots for propagation.

Blooming season: Indeterminent by seasons. By using leaf cutting propagation, some control of vegetative growth can be maintained to develop size of plant before flowering occurs.

Foliage: Would be considered average quantity for this type begonia.

Size: Leaves are large—12 cm. wide and 14 cm. long on plants grown under commercial practices in Ashtabula, Ohio.

Shape: Cordate.

Texture: Smooth, waxy, thick, extreme protrusion of veins on underside of leaf.

Margin: Finely serrated, edges of leaves roll under.

Color: Young—upperside green 137A–B, underside approximately 147C, mature upperside between 137A and 147A; underside approximately 147C.

Disease resistance: Apparently immune to mildew when grown in areas of mildew infected plants. Sightly susceptible to *Xanthomonas begoniae*.

FLOWERS

Borne: On compound cyme; the individual flower stems will usually arch because of the weight of the very large flowers. Plants have been observed to be in flowering state 12 months.

Quantity: Considered below average for this type of begonia.

Buds: Flat—approximately 12–15 mm. in diameter before opening, reverse nearly white turning to pale pink when opened.

Tepals: Edges serrated, ruffled, center tepals swirled, pink classified as slightly lighter than red-purple 58–C–D.

I claim:

1. A new and distinct cultivar of begonia plant particularly characterized by the combined characteristics of relatively large flower size, double flower form and light pink flower color; ruffled tepals and "flower-in-flower" effect of individual flowers; propagation by leaf cuttings that develop vegetative adventitious shoots; vigorous stems that provide upright growth; excellent foliage which is resistant to powdery mildrew and by its excellent keeping qualities of tepals.

No references cited.

ROBERT E. BAGWILL, Primary Examiner